(12) United States Patent  
Vodyanoy et al.

(10) Patent No.: US 7,688,505 B2
(45) Date of Patent: Mar. 30, 2010

(54) SIMULTANEOUS OBSERVATION OF DARKFIELD IMAGES AND FLUORESCENCE USING FILTER AND DIAPHRAGM

(75) Inventors: Vitaly Vodyanoy, Auburn, AL (US); Oleg Pustovyy, Auburn, AL (US)

(73) Assignee: Auburn University, Auburn, AL (US)

( * ) Notice: Subject to any disclaimer, the term of this patent is extended or adjusted under 35 U.S.C. 154(b) by 265 days.

(21) Appl. No.: 11/636,107

(22) Filed: Dec. 8, 2006

(65) Prior Publication Data

US 2007/0139764 A1 Jun. 21, 2007

Related U.S. Application Data

(60) Provisional application No. 60/749,175, filed on Dec. 9, 2005.

(51) Int. Cl.
G02B 21/06 (2006.01)
G02B 21/00 (2006.01)

(52) U.S. Cl. .................... 359/387; 359/368; 359/385

(58) Field of Classification Search ......... 359/368–390, 359/738–740
See application file for complete search history.

(56) References Cited

U.S. PATENT DOCUMENTS

| 1,544,973 A | 7/1925 | Ghadiali | |
|---|---|---|---|
| 1,613,583 A | 1/1927 | Berek | |
| 1,943,510 A | 1/1934 | Bauersfeld et al. | |
| 1,951,636 A | 3/1934 | Straubel | |
| 1,996,920 A | 4/1935 | Hauser | |
| 2,129,562 A | 9/1938 | Brueck | |
| 2,130,494 A | 9/1938 | Heine | |
| 2,642,775 A | 6/1953 | Rooney | |
| 2,674,157 A | 4/1954 | Heine | 88/39 |
| 3,666,362 A | 5/1972 | Change | 356/88 |
| 3,825,336 A | 7/1974 | Reynolds | |
| 3,930,713 A * | 1/1976 | Stankewitz et al. | 359/387 |
| 4,109,304 A | 8/1978 | Khavalovsky et al. | |
| 4,246,488 A | 1/1981 | Hura | 250/513 |
| 4,317,613 A | 3/1982 | Grosser | 350/89 |
| 4,687,304 A | 8/1987 | Piller et al. | 350/526 |

(Continued)

FOREIGN PATENT DOCUMENTS

DE    31 00 662 A1    1/1981

(Continued)

OTHER PUBLICATIONS

George E. Cragg et al., "Lateral Resolution Enhancement with Standing Evanescent Waves", Jan. 1, 2000, pp. 46-48, Optics Letters, Optical Society of America.

(Continued)

*Primary Examiner*—Thong Nguyen
(74) *Attorney, Agent, or Firm*—Haverstock & Owens LLP

(57) ABSTRACT

An annular diaphragm and filter used for the simultaneous observation of darkfield images and fluorescence. The diaphragm has a variable diameter controlled by a lever and a removable filter. The diaphragm is used to adjust the amount of unfiltered incident light which produces darkfield images when directed on a sample. The removable filter is used to filter light to a particular frequency for producing fluorescence images. An Acousto-Optical Tunable Filter, or other such tunable filter may be used with the diaphragm. A method of using the diaphragm and filter is also disclosed.

25 Claims, 10 Drawing Sheets

U.S. PATENT DOCUMENTS

| | | | | |
|---|---|---|---|---|
| 4,737,022 A * | 4/1988 | Faltermeier et al. | ......... | 359/387 |
| 4,843,528 A | 6/1989 | Pearce-Harvey et al. | | |
| 4,894,760 A | 1/1990 | Callahan | ..................... | 362/293 |
| 4,974,094 A | 11/1990 | Morito | ........................ | 358/225 |
| 5,113,332 A | 5/1992 | Richardson | ................. | 362/282 |
| 5,325,231 A | 6/1994 | Tamura et al. | | |
| 5,394,268 A | 2/1995 | Lanni et al. | .................. | 359/386 |
| 5,400,135 A | 3/1995 | Maeda | ........................ | 356/237 |
| 5,452,054 A | 9/1995 | Dewa et al. | .................... | 355/67 |
| 5,734,498 A | 3/1998 | Krasieva et al. | ............. | 359/387 |
| 5,820,250 A | 10/1998 | Betts et al. | ................... | 362/216 |
| 5,841,577 A | 11/1998 | Wachman et al. | ........... | 359/386 |
| 6,002,484 A | 12/1999 | Rozema et al. | | |
| 6,004,001 A | 12/1999 | Noll | ........................... | 362/30 |
| 6,101,037 A | 8/2000 | Park et al. | .................... | 359/618 |
| 6,181,471 B1 | 1/2001 | Miyoshi | ...................... | 359/388 |
| 6,597,499 B2 | 7/2003 | Kawano et al. | | |
| 6,628,385 B1 | 9/2003 | Osipchuk et al. | ............ | 356/318 |
| 6,633,375 B1 | 10/2003 | Veith et al. | | |
| 6,690,509 B2 | 2/2004 | Vodyanoy et al. | ........... | 359/368 |
| 6,704,140 B1 | 3/2004 | Richardson | ................. | 359/387 |
| 6,755,555 B2 | 6/2004 | Bloom et al. | ............... | 362/293 |
| 6,812,446 B2 | 11/2004 | Kreh | ........................ | 250/201.3 |
| 6,839,166 B2 | 1/2005 | Fukushima et al. | ......... | 359/368 |
| 6,865,013 B2 | 3/2005 | Vodyanoy et al. | ........... | 359/305 |
| 6,883,952 B2 | 4/2005 | Sander | | |
| 6,947,127 B2 | 9/2005 | Wolleschensky et al. | ...... | 356/73 |
| 2001/0003489 A1 | 6/2001 | Shiba et al. | | |
| 2002/0088952 A1 | 7/2002 | Rao et al. | .............. | 250/559.45 |
| 2002/0135871 A1 | 9/2002 | Vodyanoy et al. | ........... | 359/389 |
| 2003/0086163 A1 | 5/2003 | Aono et al. | .................. | 359/388 |
| 2003/0090792 A1 | 5/2003 | Kenny et al. | | |
| 2004/0239797 A1 | 12/2004 | Masuda | ....................... | 348/362 |
| 2004/0258405 A1 | 12/2004 | Shiratori et al. | ............. | 396/458 |
| 2004/0262529 A1 | 12/2004 | Yoshida et al. | .............. | 250/372 |
| 2005/0211912 A1 | 9/2005 | Fox | | |
| 2005/0237605 A1 | 10/2005 | Vodyanoy et al. | | |
| 2005/0238347 A1 | 10/2005 | Oh | ............................. | 396/449 |
| 2006/0001973 A1 | 1/2006 | Peterson et al. | ............. | 359/618 |
| 2006/0023301 A1 | 2/2006 | Dietrich et al. | | |
| 2007/0014002 A1 | 1/2007 | Vodyanoy et al. | | |
| 2007/0041109 A1 | 2/2007 | Brehm et al. | | |
| 2007/0242336 A1 | 10/2007 | Vodyanoy et al. | | |

FOREIGN PATENT DOCUMENTS

| | | | | |
|---|---|---|---|---|
| DE | 3409657 | * | 9/1985 | ................. 359/387 |
| JP | 3-266809 | * | 11/1991 | ................. 359/387 |
| JP | 5-346532 | | 12/1993 | |
| JP | 9-210906 | * | 8/1997 | ................. 359/387 |
| JP | 2002-202459 A | | 7/2002 | |

OTHER PUBLICATIONS

Vitaly Vodyanoy, "High Resolution Light Microscopy of Live Cells", May 2005, pp. 26-28 & 17, Microscopy Today.

Xiaolin Nan et al., "Lights up Lipids in Living Cells", Reprinted from the Aug. 2004 issue of Biophotonics International, pp. 1-4, CARS Microscopy, Live Cell Imaging, A Laurin Publication Biophotonics International.

Tim Richardson, "Test Slides: Diatoms to Divisions—What Are You Looking At? Part I", pp. 1-6, Bio-Microtech Inc, Umt 4.670 Hardwick Road, Ontario, L7E 5TL, Canada.

Albert H. Coons, Hugh J. Creech and R. Norman Jones (Introduced by: J.F. Enders), "Immunological Properties of an Antibody Containing a Flourescent Group", pp. 200-203, From the Department of Bacteriology and Immunology, Harvard Medical School, and the Chemical Laboratory, Harvard University.

Ji-Xin Cheng and X. Sunney Xie, "Coherent Anti-Stokes Raman Scattering Microscopy: Instrumentation, Theory, and Applications", Jun. 14, 2003; In Final Form: Oct. 2, 2003, published on the web Dec. 25, 2003, pp. 827-840, J. Phys. Chem. B 2004, Department of Chemistry and Chemical Biology, Harvard University, 12 Oxford Street, Cambridge, Massachusetts 02138.

Mathias Flörsheimer, Christof Brillert, and Harold Fuchs, "Chemical Imaging of Interfaces by Sum Frequency Microscopy", Received Nov. 5, 1998. In final From Jan. 14, 1999 Langmuir 1999, Published on the web Feb. 24, 1999, pp. 5437-5439, Physical Institute, University of Münster, Wilhelm-Klemm-Strasse 10, D-48149 Münster, Germany.

Lord Rayleigh, Sec. R.S., "XV. On the Theory of Optical Images, with Special Reference to the Microscope", 1896, vol. XLII, pp. 167-195, Lord Rayleigh. Philosophical Magazine.

Maksymilian Pluta, "Advanced Light Microscopy", 1989, pp. 211-216 vol. 2, Elsevier Amsterdam-Oxford-New York-Tokyo PWN-Polish Scientific Publishers, Warszawa.

Arnold Vinrub, Oleg Pustovyy, and Vitaly Vodyanoy "Resolution of 90 nm λ/5) in an optical transmission microscope with an annular condenser", Received Jun. 12, 2006, posted Jul. 16, 2006, (Doc ID 71923) Published Sep. 11, 2006, Oct. 1, 2006, vol. 31 No. 19, pp. 2855-2857, Department of Anatomy, Physiology and Pharmacology, College of Veterinary Medicine, Auburn University, Auburn, Alabama 36849.

JiXin Cheng, Y.Kevin Jia, Gengfeng Zheng, and X. Sunney Xie, "Laser-Scanning Coherent Anti-Stokes Raman Scattering Microscopy and Applications to Cell Biology", Jul. 2002, vol. 83, pp. 502-509 Department of Chemistry and Chemical Biology, Harvard University, Cambridge, Massachusetts 02138, and SEG, Olympus America Inc., Biophysical Journal Department, Melville, New York 11747-3157 USA.

Barbara Foster, "Focus on Microscopy: A Technique for Imaging Live Cell Interactions and Mechanisms", Nov. 2004, Reprinted from American Laboratory, 5 pages.

Frithjof A.S. Sterrenburg, "Crystal Palaces—Diatoms for Engineers", pp. 1-14, Westerstraat 47, 1655LC Sijbekarspel The Netherlands, fass@wxs.nl. Research Associated, National Natural History Museum "Naturalis", Leyden, The Netherlands).

Hecht, Eugene, "Geometrical Optics," Chapter 5, p. 156, Adelphi University, 2002 Pearson Education.

* cited by examiner

SIMULTANEOUS OBSERVATION OF DARKFIELD IMAGES AND FLUORESCENCE USING FILTER AND DIAPHRAGM

RELATED APPLICATIONS

The present application claims priority to U.S. Provisional Patent Application 60/749,175, filed on Dec. 9, 2005, and entitled "Simultaneous Observation of Darkfield Images and Fluorescence Using Filter and Diaphragm" to the same inventor under U.S.C. section 119(e). This application incorporates U.S. Provisional Patent Application 60/749,175, filed on Dec. 9, 2005, and entitled "Simultaneous Observation of Darkfield Images and Fluorescence Using Filter and Diaphragm" to the same inventor by reference in its entirety.

FIELD OF THE INVENTION

The present invention relates generally to the field of optical microscopy. More particularly, the invention relates to the simultaneous observation of Darkfield Images and Fluorescence using a filter and a diaphragm in an optical microscope.

BACKGROUND

All living creatures including humans are made of cells. The majority of life forms exist as single cells that perform all functions to continue independent life. A number of cells, cell organelles, bacteria and viruses are too small to be seen with traditional optical microscopes. To view cellular life, the microscope must have high resolution.

Currently there are a few microscopes which offer very fine resolution. Examples include "High-Resolution Optical Microscope" described in U.S. Pat. No. 6,690,509 and the "High Resolution Optical Microscope" described in U.S. patent application Ser. No. 11/607,269, filed on Dec. 1, 2006.

Electron microscopes are another example. However, in using electron microscopes, the specimen must be prepared by high-vacuum dehydration and is subjected to intense heat by the electron beam, making observation of living specimens impossible. The sample preparation for electron microscopy requires living cells to be killed, frozen, dehydrated and impregnated with heavy metals. The dehydration process also alters the specimen, leaving artifacts and cell damage that were not present in nature. These procedures, together with electron beam damage caused during the observation of the cells creates the possibility that some components of the cell may be lost or destroyed. Also, in order to view the steps in a biological process, dozens of specimens must be viewed at various stages in order to capture each desired step. Further, specimen preparation for electron microscopes can take up to two hours each.

The high cost of an electron microscope represents another barrier to its use in the life sciences. Electron microscopes are large and often require an entire room. The operation and adjustment of an electron microscope also requires highly skilled technicians.

The ultraviolet microscope offers finer resolution and better magnification than an ordinary light microscope, but it has serious disadvantages for the study of living specimens. Ultraviolet light damages or kills many kinds of living biological specimens, making observation impossible. In ultraviolet microscopy, specimens are often stained with a fluorescent dye. Many fluorescent dyes bind strongly to elements such as enzymes within living cells, changing their qualities and significantly altering the cellular biochemistry. Other dyes produce too much fluorescence or absorb too much of the ultraviolet light to be useful.

Like electron microscopes, the operation of an ultraviolet microscope requires a great deal of skill. Because ultraviolet light damages the human eye, the image can only be observed by ultraviolet video cameras or specially-equipped still cameras. Also, the quartz optics required for ultraviolet microscopes are much more expensive than the glass components used in visible light microscopes.

The electron and ultraviolet microscopes available today do not offer a technique for observing living, unaltered biological specimens in real time. The damage from the electronic beam, from fixing, freezing, exposure to ultraviolet light, and other procedures which occur during observation limits the processes which can be seen by such devices. For example, the phenomenon of cellular transport cannot be observed in non-living cells by these known devices. Other examples of phenomena which cannot be directly observed by electronic microscopes include: streaming, Brownian motion, diffusion, phagocytosis, pinocytosis, mitosis, immuno-fluorescence, and cell interactions.

It is important for scientists in the biomedical community to observe these living cells and their processes in order to better understand the cellular world. Currently, the behavior cells and the phenomena responsible can only be inferred. These processes can only be studied in depth while they are occurring and while the cells are alive. Observing live cellular activity is needed to more completely understand such processes as gene therapy, artificial insemination, new drug development, cell culturing and cloning, cell regeneration, implantation, bio-detection, and biotherapeutics, amongst others. Observing very small, live cells at a high resolution, with a high contrast could possibly lead to the development of treatments to diseases and other health problems.

Fluorescent microscopes can be useful to the study of bacteria, animal, and plant cells, as they show primary fluorescence (autofluorescence) when illuminated with ultraviolet light. A fluorescent microscope is a microscope for observation of small objects by a light of their fluorescence. Fluorescence is most commonly generated by excitation with light. The emitted fluorescence light normally has a longer wavelength than that of the exciting light. Three important steps can divide the process of fluorescence. First, a molecule is excited by an incoming photon during the first few femtoseconds. During the next few picoseconds, the molecule goes through a vibrational relaxation of an excited state electron to the lowest energy level of the intermediate states. Finally, emission of a longer wavelength photon and recovery of the molecule into the ground state occurs during a few nanoseconds. The whole process from excitation of the molecule by an excitation light (EL) to emission of a longer wavelength fluorescent light (FL) is used for fluorescent microscopy.

The main function of a fluorescent microscope is to illuminate a sample with light of a specific wavelength (excitation light), excite the molecules of the sample with a fluorescent light, and then separate a weak emitted fluorescence from the excitation light, so that the emitted fluorescence can be observed. A special light source and the presence of two filters typically characterize the optical pathways of the fluorescent microscope: one filter is placed before a condenser and the other filter is placed after the objective. The first filter transmits only exciting radiation, and the second filter transmits only emitted fluorescent light. Thus, the excitation light incident on a sample is removed, while fluorescent light is directed to the observer's eye, or to a recording device. The light source should provide a short-wavelength light such as UV and/or blueviolet light. Currently, there are two different optical designs of fluorescent microscopes in common usage: one uses a transmitted light illumination ("dia-fluorescence microscopy") and the other employs a reflected light ("epi-fluorescence microscopy").

The light of the wavelengths required for fluorescence excitation are selected by an excitation filter, which transmits only exciting light and suppresses light of all other wavelengths. A certain part of the exciting light is adsorbed by the sample and almost instantaneously re-emitted at longer wavelengths as fluorescence light. A barrier filter transmits the fluorescence light (emission light). The rest of the excitation light which passes through or reflects from the sample is absorbed by the barrier filter. As a result, a color image of the sample is observed (or recorded) against a dark background.

Early fluorescence microscopes were generally brightfield transmitted light microscopes equipped with excitation and barrier filters. The transmitted light fluorescence microscope was greatly improved by using a darkfield condenser. A darkfield condenser projects light onto the sample at oblique angles, which prevents excitation light from directly entering the objective. Certain difficulties of the conventional transmitted light fluorescence light microscope made the reflected light fluorescence microscope the instrument of choice by many users.

Both the brightfield and the darkfield techniques has proven valuable in various applications, but also have certain disadvantages. It would be beneficial to be able to vary the wavelength and the amount of light which is directed to a sample to be able to view both darkfield images and fluorescent images simultaneously.

SUMMARY OF THE DISCLOSURE

The present invention discloses a method and apparatus for simultaneous observation of high resolution darkfield images and fluorescence. The apparatus includes a variable diaphragm and a filter. The diaphragm and filter are separate, or alternatively, the filter is housed in the diaphragm. In some embodiments, the diaphragm and filter are positioned before a flat mirror and convex mirror of an illumination system and after a light source, light guide and collimating lens of an illumination system.

In some embodiments of the invention, the diaphragm includes a center portion for a filter. The filter allows only a frequency that produces fluorescence and the periphery portion allows all other frequencies that produce scattered or darkfield images. In some embodiments, the center portion passes a frequency (F1), which is a known frequency that produces a fluorescent image from a particular sample.

In some embodiments of the present invention, the diaphragm is a variable diaphragm which varies in size. Changing the size allows more or less light of a certain frequency to pass through the diaphragm. In some embodiments, the variable diaphragm includes a rotate lever for opening and for closing the diaphragm to allow those frequencies that expose more or less of a darkfield image. When opened, the diaphragm allows more light through which results in more scattered light. When the diaphragm is closed less scattered light results.

It is important to be able to vary the amount of light that reaches the sample. Certain samples will only emit a small amount of flourescent light when excited. In this case, only a small amount of unfiltered light is allowed to enter the observation lens or else the fluorescent image will be washed out. In other cases this is not a problem, and a lot of unfiltered light may be allowed to produce brighter images.

In some embodiments of the present invention, the filter is a special filter for filtering one particular frequency. In other embodiments, the filter is a tunable filter which is tuned to a particular voltage to filter the particular frequency needed to produce fluorescence in a given sample. In other embodiments, the filter is completely removed from the diaphragm.

BRIEF DESCRIPTION OF THE DRAWINGS

The novel features of the invention are set forth in the appended claims. However, for the purpose of explanation, several embodiments of the invention are set forth in the following figures.

DETAILED DESCRIPTION

Darkfield Microscopy and Fluorescence Microscopy techniques are similar at a basic level. Both involve shining incident light from a light source onto a sample to produce images. Both techniques effectively produce high resolution images of small specimen. The present invention allows a scientist the option of using both techniques simultaneously.

Figure 1:
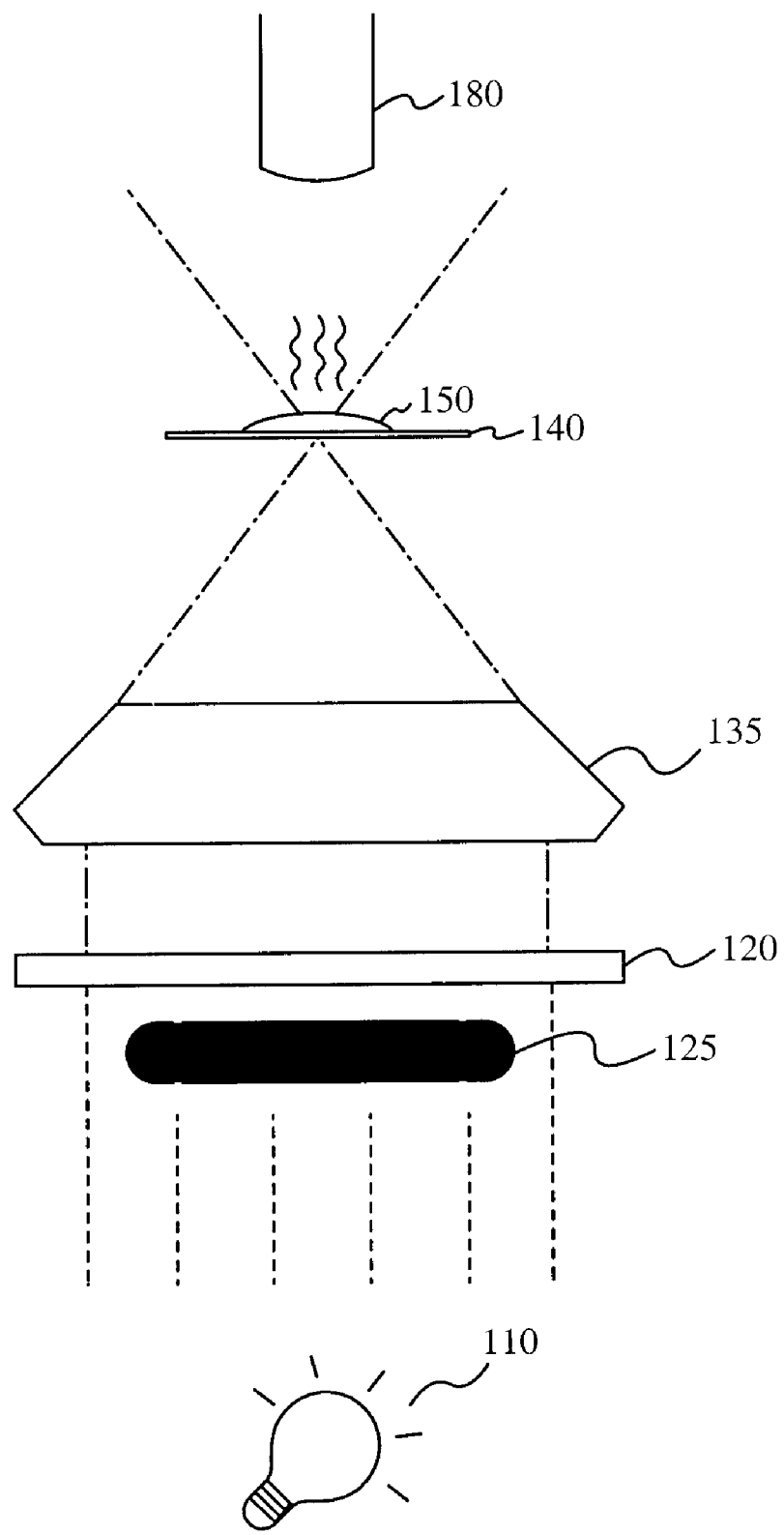
FIG. 1 illustrates the basic Darkfield microscopy technique.

The basic Darkfield Microscopy model involves directing incident light onto a sample at a certain angle. FIG. 1 illustrates the darkfield microscopy technique. A light source 110 directs light at a Darkfield Condenser 135. A central block 125 is used to block the center portion of light, such that only a hollow cylinder of light travels toward the Darkfield Condenser 135. A filter 120 may also be included to filter out certain wavelengths of incident light. The Darkfield Condenser 135 directs the light at some angle toward the slide 140 and the specimen 150. When the light enters the specimen 150, some of it is diffracted and refracted by molecules in the specimen 150. However, much of the light is unaffected and continues at the same incident angle. This latter light bypasses the observation lens 180. Light which is diffracted and refracted may change direction and be angled toward the observation lens 180. Light that enters the observation lens 180 forms an image which is viewed by a human or recorded by a camera or computer.

Fluorescent Microscopy is similar, however, the main function of a fluorescent microscope is to illuminate the sample with light of a specific wavelength (excitation light), excite a fluorescent light, and then separate the weak emitted fluorescent light from the excitation light. Fluorescence is a short time luminescence which is most commonly excited by light. When photons are directed toward a sample the energy in the photons causes the molecules in the sample to become excited. The excited state electron in the molecule jumps to the lowest energy level in the intermediate state and then goes through vibrational relaxation. Finally, the emission of a longer wavelength photon and recovery of the molecule into the ground state occurs.

Figure 2:
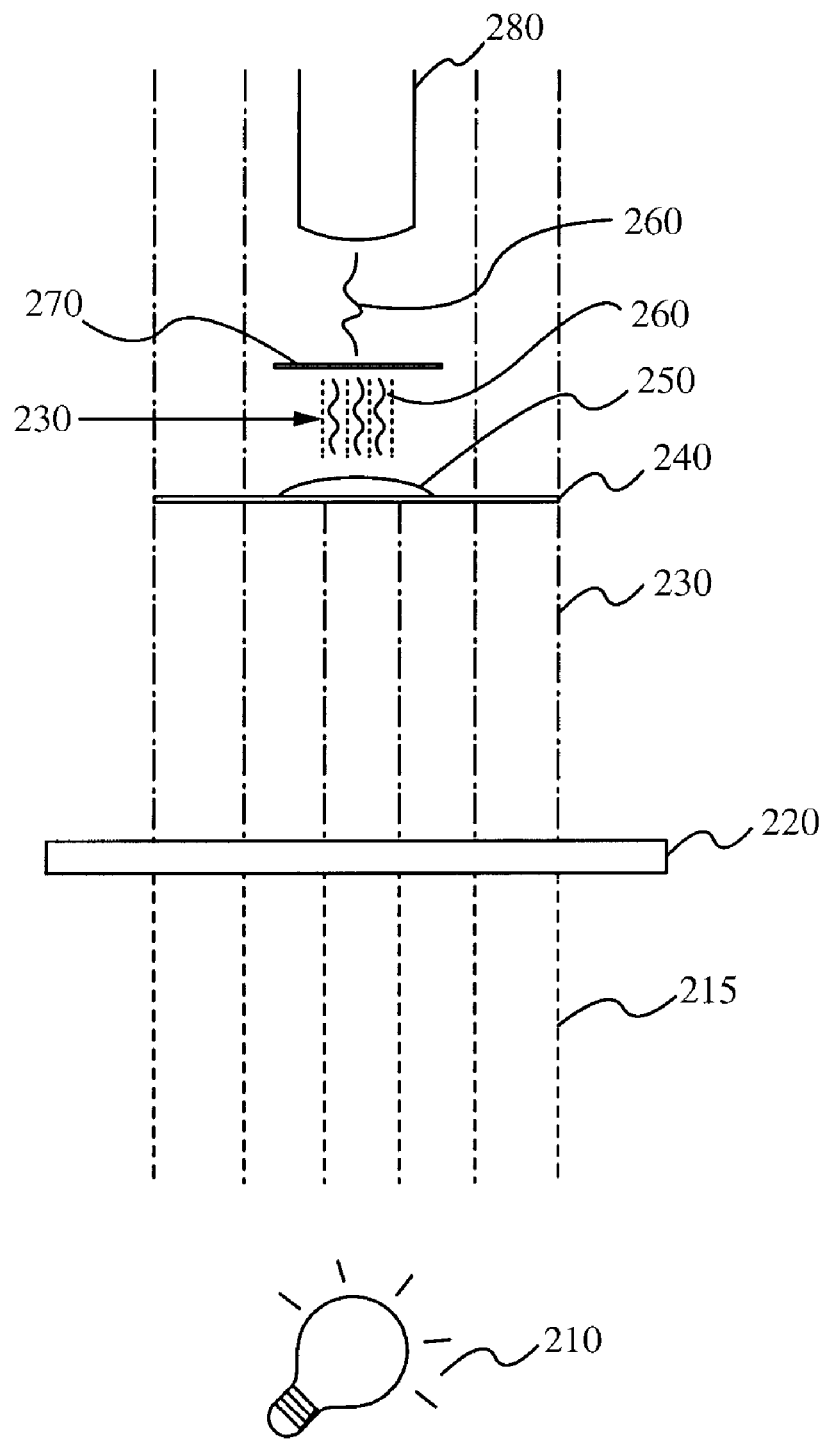
FIG. 2 illustrates the basic Fluorescent microscopy technique.

FIG. 2 illustrates the basic setup used in fluorescent microscopy. A special light source 210 is used which emits light 215. A first filter 220 filters the light 215 from the light source 210 resulting in Excitation Light 230 with the proper wavelength to cause excitation in a specimen 250. This Excitation Light 230 is directed toward a slide 240 containing the specimen 250. The Excitation Light 230 incident on the specimen 250 excites molecules in the specimen resulting in emitted Fluorescent Light 260 with a higher wavelength. A portion of Excitation Light 230 also passes through the specimen unaltered. A second filter 270 is a Barrier Filter used to filter the Excitation Light 230 from the Fluorescent Light 260. The filtered Fluorescent Light 260 is then observed by an observation lens 280.

Figure 3:
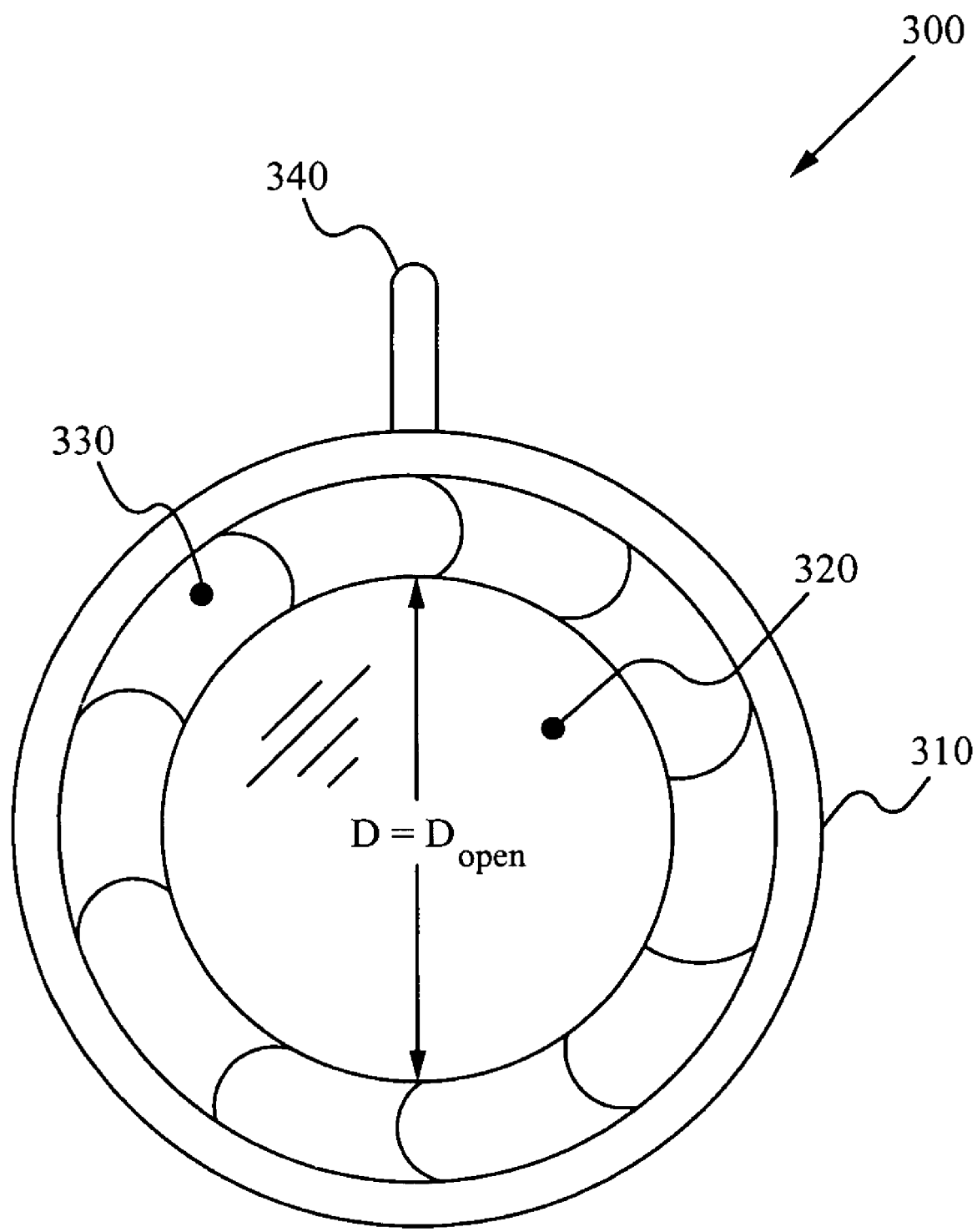
FIG. 3 is a diaphragm of the present invention, without a filter, in an open position.

FIG. 3 illustrates a diaphragm 300 of the present invention, without a fluorescent light filter, in an open position. The diaphragm 300 consists of an outside ring 310, an inside transparent surface 320 and a variable opening surface 330. The variable opening surface is able to be closed over the clear inside surface by the lever 340. Here, the variable opening surface is all the way open resulting in a light opening with diameter $D=D_{open}$. No filter is used in this diaphragm, however, in some embodiments, the clear inside surface accommodates a filter (not shown). The embodiment illustrated in FIG. 3 allows for the maximum amount of unfiltered light to pass through the diaphragm 300 without filtering light for pure fluorescent microscopy.

Figure 4:
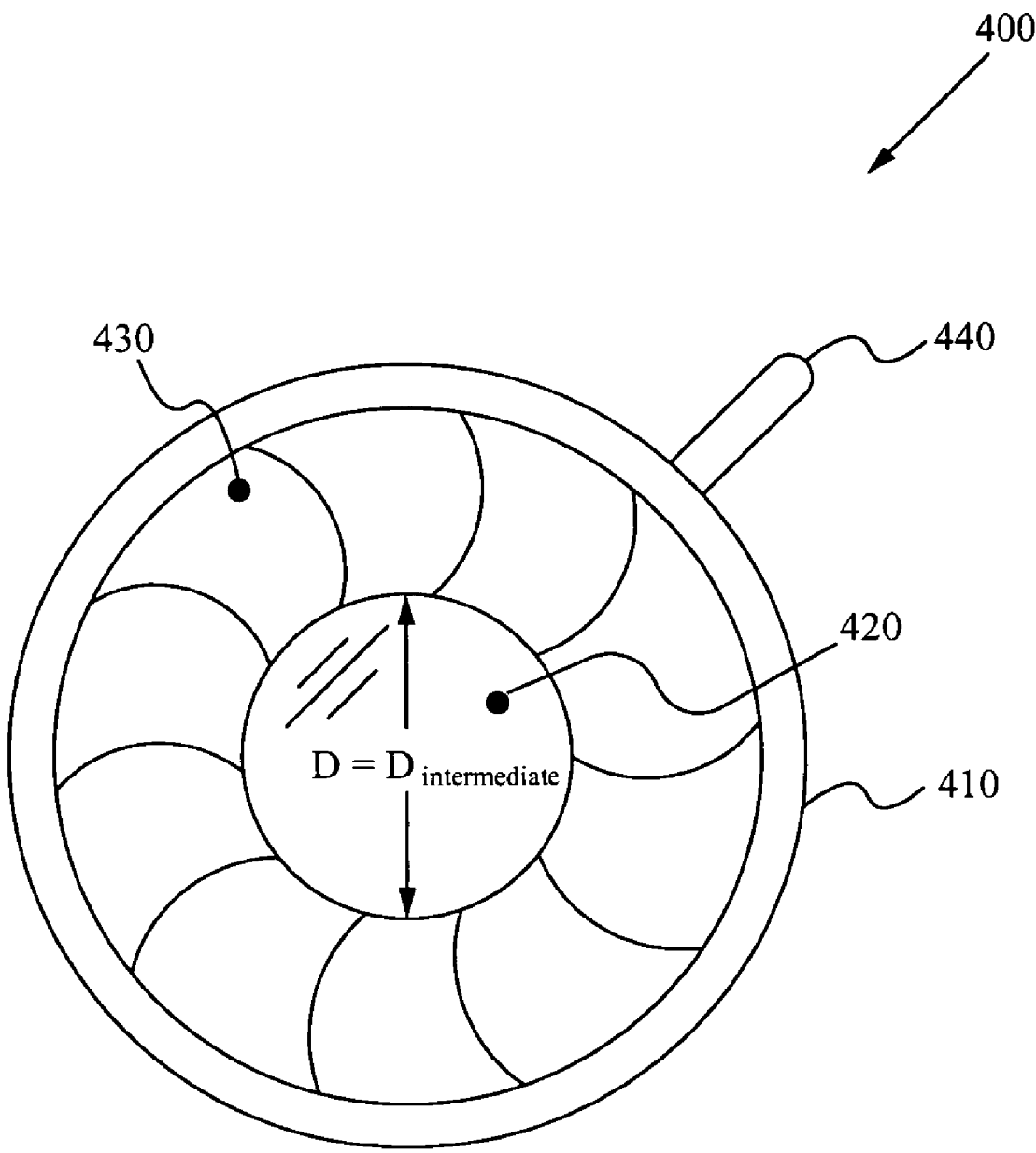
FIG. 4 is a diaphragm of the present invention, without a filter, in an intermediate position.

FIG. 4 illustrates a diaphragm 400 of the present invention, without a fluorescent light filter, in an intermediate position. The diaphragm 400 consists of an outside ring 410, an inside clear surface 420 and a variable opening surface 430. The variable opening surface 430 is able to be closed over the clear inside surface 420 by the lever 440. Here, the variable opening surface 430 is partially closed, resulting in a light opening with diameter $D=D_{intermediate}$. In some embodiments, the clear inside surface accommodates a filter (not shown). The embodiment illustrated in FIG. 4 allows less unfiltered light to pass through the diaphragm 400 than in the embodiment of FIG. 3, still without filtering light for pure fluorescent microscopy.

Figure 5:
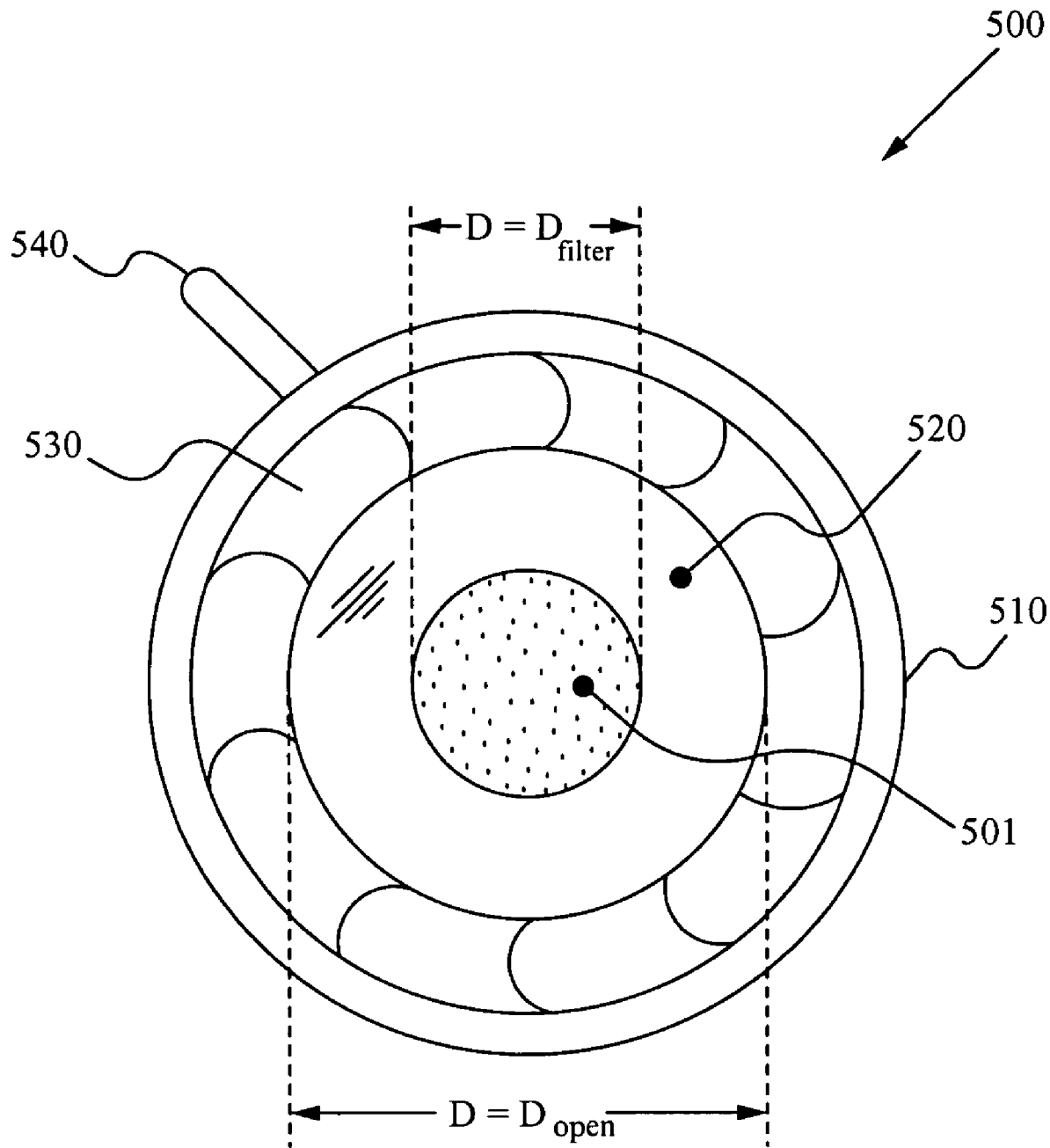
FIG. 5 is a diaphragm of the present invention, with a filter, in an open position.

FIG. 5 illustrates a diaphragm 500 of the present invention, with a fluorescent light filter 501, in an open position. The diaphragm 500 consists of an outside ring 510, an inside clear surface 520, a variable opening surface 530 and a fluorescent light filter 501 with diameter $D=D_{filter}$. The variable opening surface 530 is able to be closed over the clear inside surface 520 by the lever 540. Here, the variable opening surface 530 is partially closed, resulting in a light opening with diameter $D=D_{open}$. The embodiment illustrated in FIG. 5 allows for a wide beam of unfiltered light to pass through the diaphragm 500 while filtering the middle portion of light for pure fluorescent microscopy.

Figure 6:
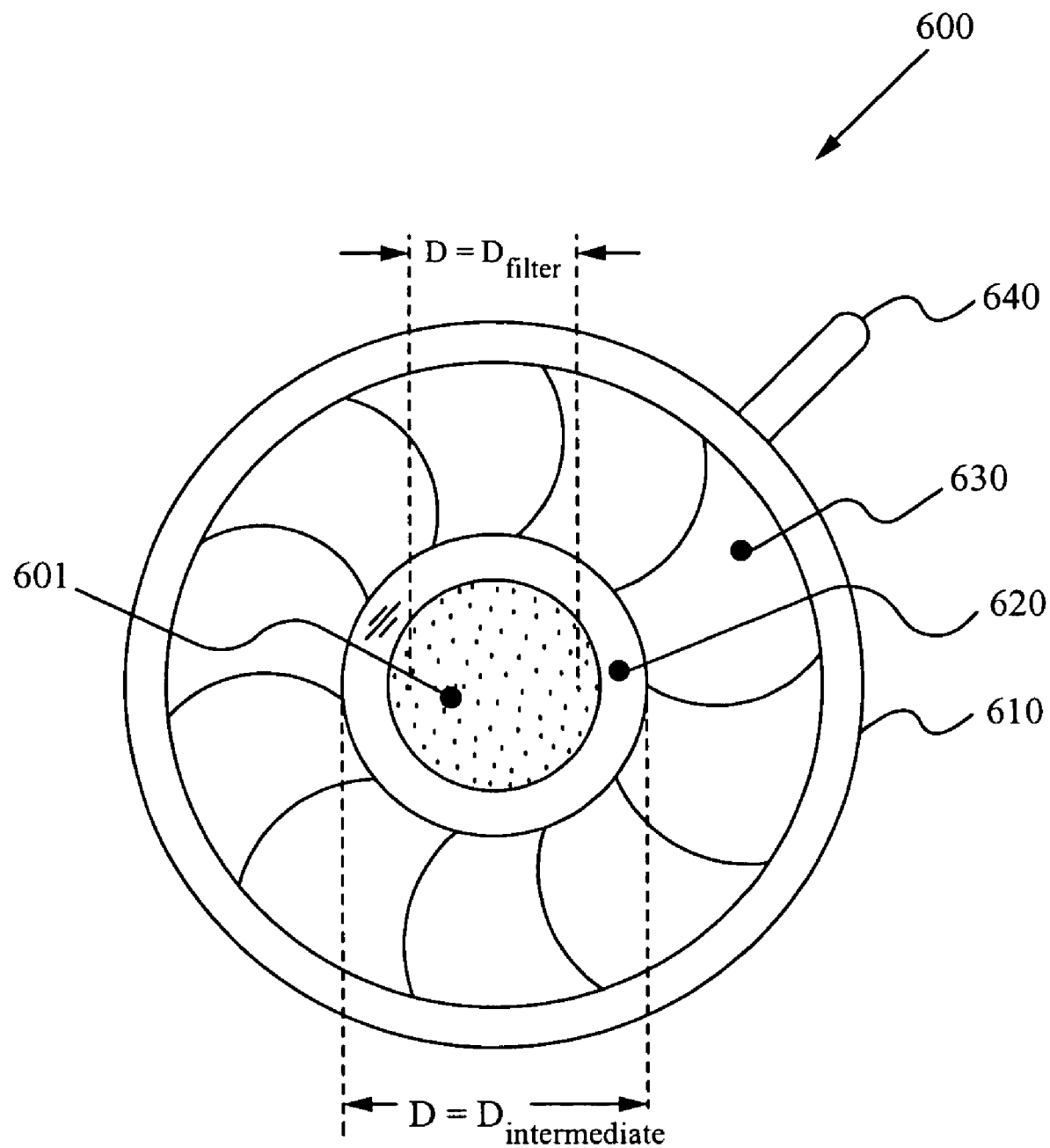
FIG. 6 is a diaphragm of the present invention, with a filter, in an intermediate position.

FIG. 6 illustrates a diaphragm 600 of the present invention including a fluorescent light filter 601, in an intermediate position. The diaphragm 600 consists of an outside ring 610, an inside clear surface 620, a variable opening surface 630 and a fluorescent light filter 601. The variable opening surface 630 is able to be closed over the clear inside surface 620 by the lever 640. Here, the variable opening surface 630 is partially closed, resulting in a light opening with diameter $D=D_{intermediate}$. The embodiment illustrated in FIG. 6 allows less unfiltered light to pass through the diaphragm 600 than in FIG. 5 while filtering the middle portion of light for pure fluorescent microscopy.

Figure 7:
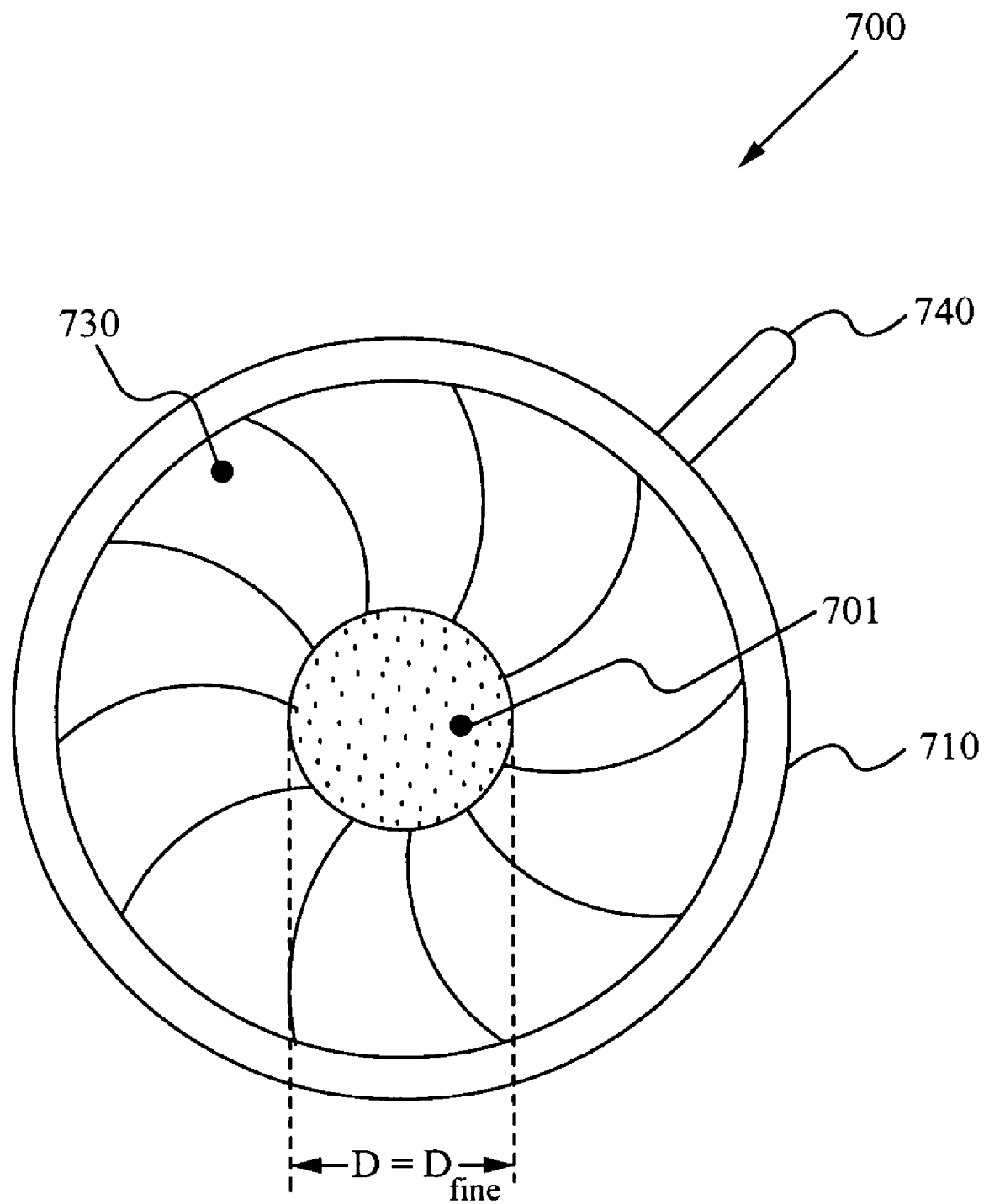
FIG. 7 is a diaphragm of the present invention, with a filter, in a closed position.

FIG. 7 illustrates a diaphragm 700 of the present invention, with a fluorescent light filter 701, in a position which completely blocks unfiltered light and also blocks some filtered light. The diaphragm 700 consists of an outside ring 710, an inside clear surface (not shown), a variable opening surface 730 and a fluorescent light filter 701. The variable opening surface 730 is able to be closed over the clear inside surface by the lever 740. Here, the variable opening surface 730 is closed to block all unfiltered light and some filtered light, resulting in a light opening with diameter $D=D_{fine}$, which is smaller than the diameter $D=D_{filter}$. The embodiment illustrated in FIG. 7 allows no unfiltered light to pass though the diaphragm 700 and a small amount of pure fluorescent light for pure fluorescent microscopy.

Figure 8:
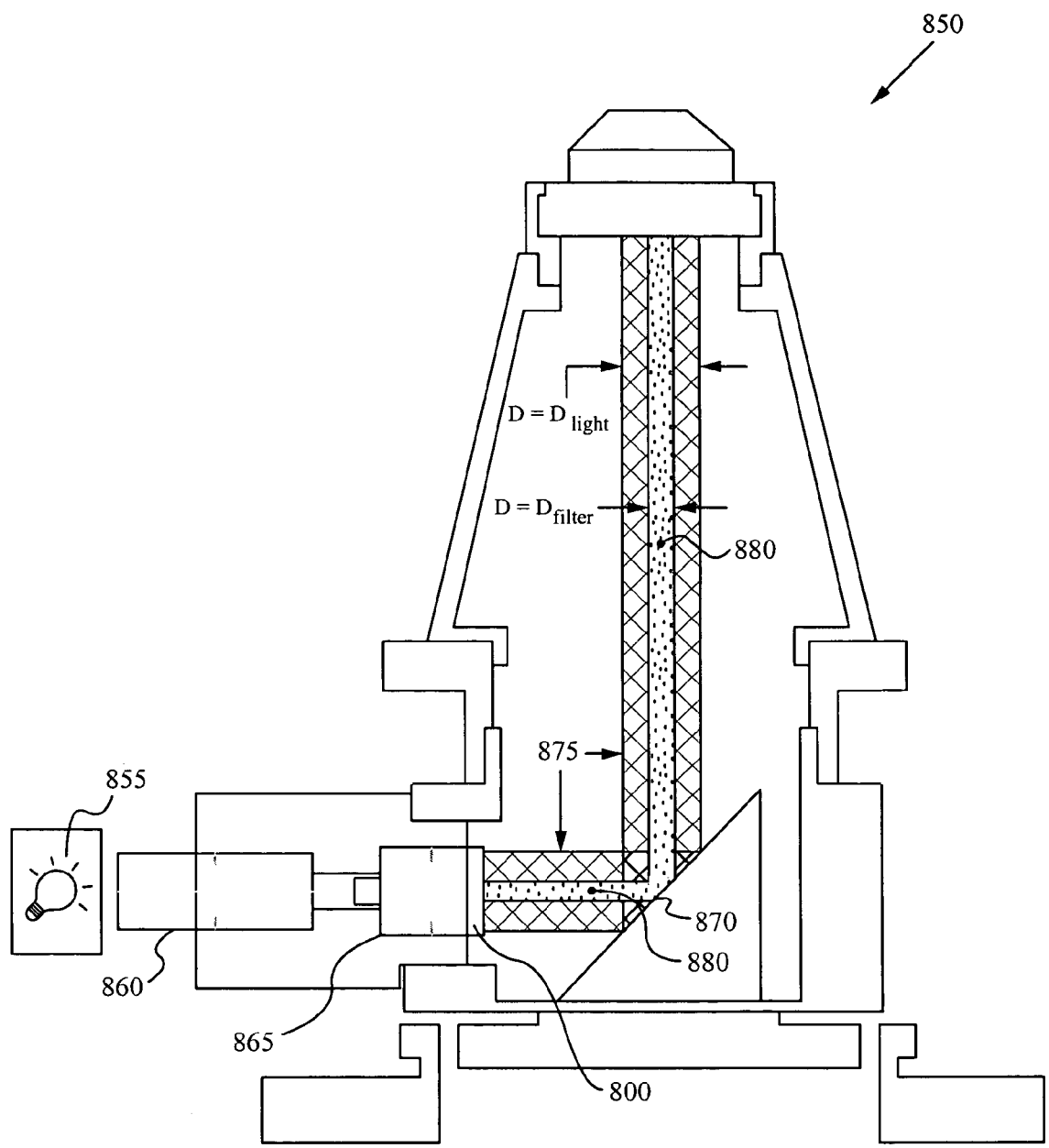
FIG. 8 is a microscope fitted with the diaphragm and filter of the present invention.

FIG. 8 illustrates a diaphragm 800 as explained above used in a microscope 850. The microscope light source 855 emits light with certain wavelengths. The light guide 860 guides that light to a light collimating device 865. The diaphragm 800 is located after the collimating device, but before the mirror 870. Light from the light source 855 is collimated and encounters the diaphragm 800. The diaphragm 800 is variable, meaning that the diaphragm 800 is able to be set to block no light, some light, or all light coming from the light collimating device 865, resulting in a beam of light 875 with the opening in the diaphragm 800 having a diameter $D=D_{light}$. Further, the diaphragm 800 may or may not include a fluorescent light filter (not shown). When no filter is used, the beam of light 875 is comprised of the same frequency light that originated at the light source 855. When a fluorescent light filter is used, the fluorescent light filter filters light of all wavelengths except particular wavelengths used for fluorescent excitation of molecules in a sample (not shown). The filtering results in the beam of light 875 having an inside beam of light 880, composed of only fluorescent wavelengths, with the same diameter as the fluorescent light filter, $D=D_{filter}$. In some embodiments, a fluorescent light filter is used and the diaphragm 800 is closed such that all light passing through the diaphragm 800 is filtered.

Figure 9:
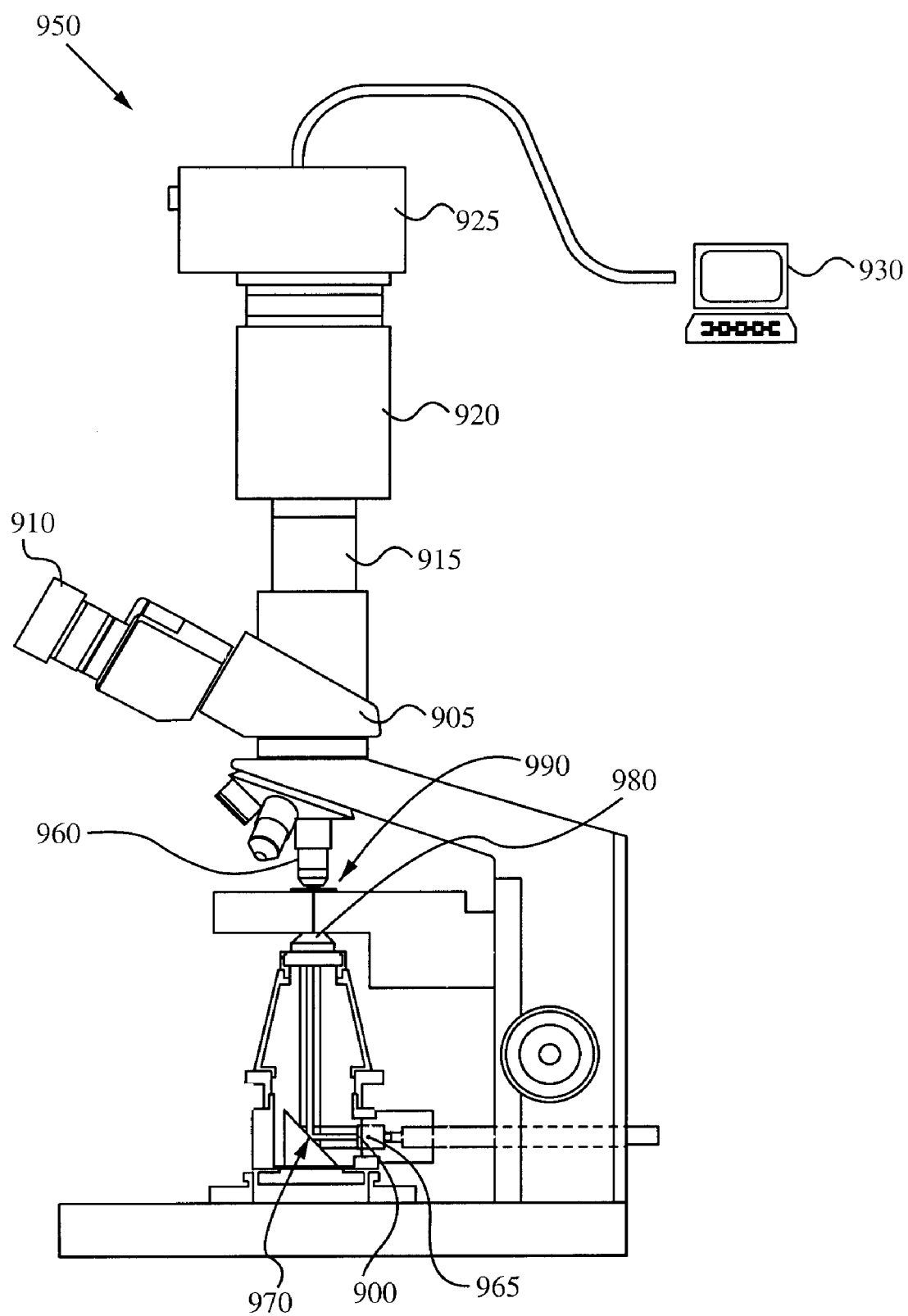
FIG. 9 is a side view of one embodiment of the present invention incorporated into a traditional research microscope.

FIG. 9 illustrates a diaphragm 900 and a fluorescent light filter (not shown), as illustrated in FIG. 8 above, combined with a traditional research microscope 950. In FIG. 9, the diaphragm 900 and the fluorescent light filter are positioned in the microscope's optical train, after the collimating device 965 and before the mirror 970. The diaphragm 900 blocks a portion of light and the fluorescent light filter filters the light. Light travels through the condenser 980, through the slide 990 and interacts with a sample. Fluorescent and scattered light travel to an objective lens 960. Light from the objective lens 960 travels into the trinocular head 905 for viewing by an eyepiece 910 and upward through an upwardly directed projection eyepiece 915. The image is magnified by a compound relay lens 920 and transmitted to a camera 925 and a computer 930.

Figure 10:
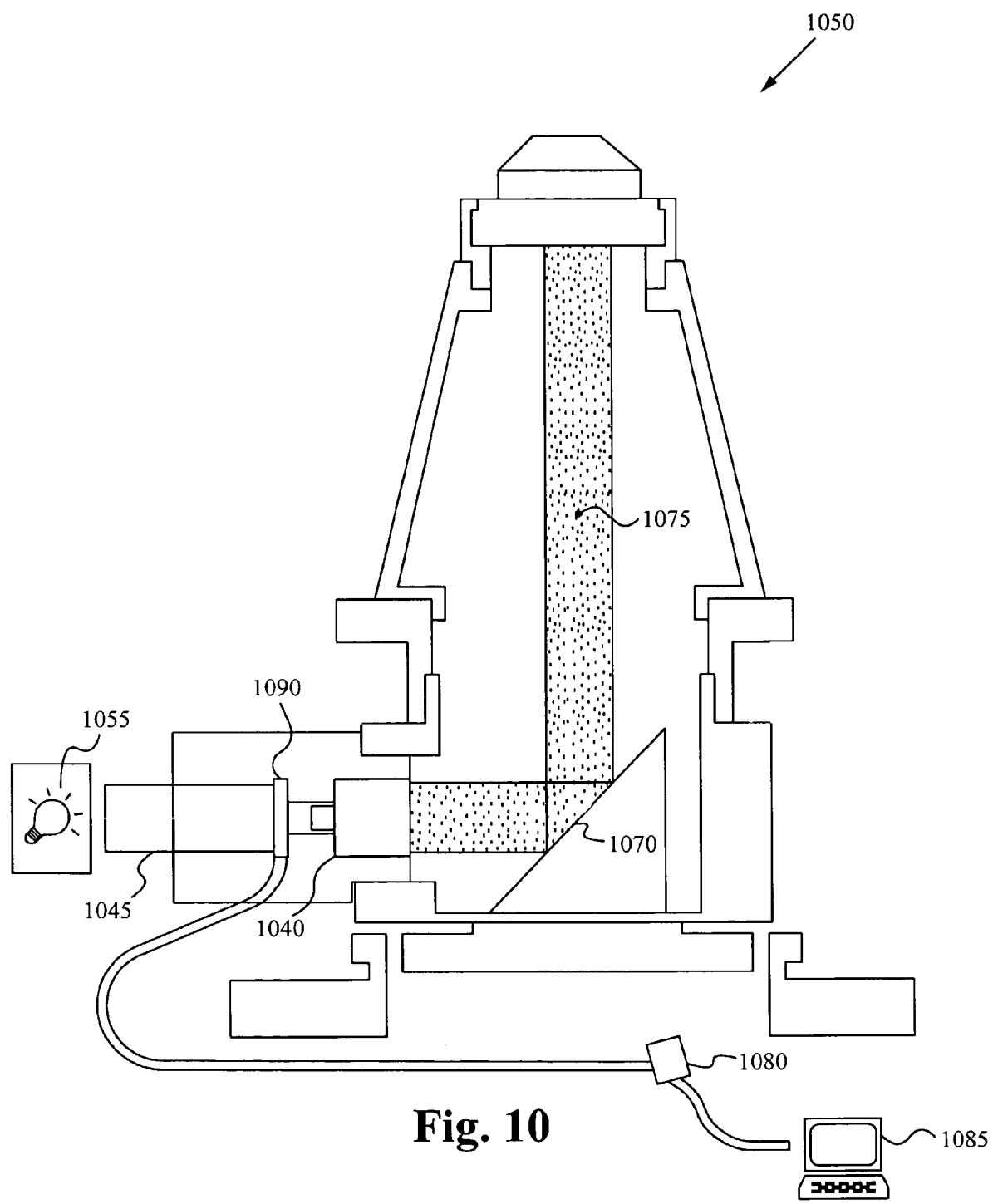
FIG. 10 is a microscope with an Acousto-Optical Tunable Filter.

In some embodiments of the present invention, the filter is a special filter for filtering one particular frequency. For example, some samples produce fluorescence when illuminated with green light. In that case, a filter is used which filters all illumination except green light, around 510 nanometers. In other embodiments, the filter is a tunable filter which is tuned to select a frequency which corresponds to a frequency which results in fluorescence for a given sample. An Acousto-Optical Tunable Filter (AOTF) is sometimes used for this purpose. An AOTF is a special crystal filter which changes the frequency of light coming through by applying a voltage to the filter. In some embodiments of the present invention, the AOTF includes an entrance port and an exit port. The entrance port receives white light in combinations of different frequencies. The exit port outputs light of certain frequencies. A change of frequency occurs by applying a voltage to the AOTF. Thus, the wavelength depends on the voltage applied to the AOTF. In some embodiments, the AOTF is driven by a computer. FIG. 10 illustrates how the present invention is used with an AOTF filter.

FIG. 10 illustrates one embodiment of the present invention using a diaphragm with an AOTF filter 1090 used in a microscope 1050. The microscope light source 1055 emits light with certain wavelengths. The light guide 1045 guides that light to an AOTF 1090 which filters the light to a particular wavelength, producing filtered light 1075. The AOTF 1090 is controlled by changing the voltage from a power supply 1080 which is controlled by a computer 1085. A light collimating device 1040 collimates the filtered light and directs it to a mirror 1070 where it is reflected up toward the sample (not shown).

In operation, the present invention allows the simultaneous observation of both darkfield and fluorescence images in a microscope. To accomplish such simultaneous observation, the amount of light that reaches the sample and the frequency of the fluorescent light must be optimized depending on the properties of the sample. The present invention allows optimization of the amount of light that reaches the sample and the frequency of the fluorescent light by controlling the diameter of the opening that light can go through and by the use of a filter. Decreasing the diameter of the diaphragm will limit the amount of light incident on the sample. Furthermore, using a filter in conjunction with the diaphragm allows a user to select both the amount of unfiltered light (if any) to direct to the sample and also the frequency and diameter of the filtered light beam.

Controlling the diameter of the diaphragm helps allow the simultaneous observation of both darkfield and fluorescence images in a microscope. For instance, certain samples will only emit a small amount of flourescent light when excited. In this case, only a small amount of unfiltered light is allowed to enter the observation lens or else the fluorescent image will be washed out by the excess light. Alternatively, sometimes the sample produces strong fluorescence and bright fluorescent images. In such a case it is possible to allow a lot of unfiltered light through the diaphragm, enabling brighter images.

Optimizing the setup also requires using a frequency filter which filters light from a light source and only allows light having the optimal frequency through to excite fluorescence in a sample. In some embodiments of the present invention, the filter is a special filter for filtering one particular frequency. In other embodiments, the filter is a tunable filter which is tuned to filter the particular frequency needed to produce fluorescence in a given sample. An Acousto-Optical Tunable Filter (AOTF) is used in some embodiments. The AOTF tunes the filter by passing a particular voltage through the filter. In other embodiments, the filter is completely removed from the diaphragm.

Another advantage of the present invention is that the necessary components are easy to use. The diaphragm of the present invention is simple to adjust which avoids requiring a user to possess special training. In some embodiments, fine-tuning the diameter of the opening is accomplished by simply moving a lever, allowing adjustment without disassembling the whole optics train. Furthermore, using an AOTF filter also avoids having to manually change filters in an optics train to filter some particular frequency, rather a user simply changes the voltage on a voltmeter to tune the AOTF filter and optimize the frequency based on the properties of the sample. Other advantages will be readily apparent to those ordinarily skilled in the art.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, it will be apparent to one of ordinary skill in the art that the device and method of the present invention could be implemented in several different ways and have several different appearances.

What is claimed is:

1. A diaphragm for use with a microscope comprising:
    a center portion for passing light having wavelengths that produce fluorescence;
    an outer portion for passing light to produce scattered light; and
    an adjustable portion for varying a ratio of fluorescence to scattered light.

2. The diaphragm for use with a microscope according to claim 1, wherein the adjustable portion is adjusted by a lever.

3. The diaphragm for use with a microscope according to claim 1, wherein the center portion comprises a removable filter.

4. The diaphragm for use with a microscope according to claim 3, wherein the filter filters light of one particular wavelength from white light.

5. The diaphragm for use with a microscope according to claim 1, wherein the light passing through the center portion and the light passing through the outer portion interact with a sample, producing a darkfield image and a fluorescent image when the light is observed with an objective lens of a microscope.

6. A direct-view light optical microscope comprising:
    an illumination system for producing light; and
    a diaphragm comprising:
        a center portion for passing light having wavelengths that produce fluorescence;
        an outer portion for passing light to produce scattered light; and
        an adjustable portion for varying a ratio of fluorescence to scattered light.

7. The direct-view light optical microscope according to claim 6, wherein the adjustable portion is adjusted by a lever.

8. The direct-view light optical microscope according to claim 6, wherein the center portion comprises a removable filter.

9. The direct-view light optical microscope according to claim 6, wherein the filter filters light of one particular wavelength from white light.

10. The direct-view light optical microscope according to claim 6, further comprising an Acousto-Optical Tunable Filter, wherein the Acousto-Optical Tunable Filter filters incident light, resulting in filtered light, and wherein the Acousto-Optical Tunable Filter is connected to a power source for providing a voltage, wherein a wavelength of the filtered light is tuned by changing the voltage supplied to the Acousto-Optical Tunable Filter, and wherein the resulting light is tuned to a desired wavelength.

11. The direct-view light optical microscope according to claim 6, wherein the light passing through the center portion and the light passing through the outer portion interact with a sample, producing a darkfield image and a fluorescent image when the light is observed with an objective lens of a microscope.

12. The direct-view light optical microscope according to claim 6, further comprising a stage with a sample and an objective lens.

13. The direct-view light optical microscope according to claim 12, wherein the light passing though the center portion and the light passing through the outer portion are directed to the stage with the sample, interacting with the sample, producing a darkfield image and a fluorescent image, and further wherein the darkfield image and the fluorescent image are simultaneously observed with the objective lens.

14. A direct-view light optical microscope comprising:
an illumination system for producing light;
a light guide;
a collimating light adaptor; and
a diaphragm comprising:
 a center portion comprising a filter for passing light having wavelengths that produce fluorescence;
 an outer portion for passing light to produce scattered light; and
 an adjustable portion for varying a ratio of fluorescence to scattered light;
wherein the light guide directs the light to the collimating adaptor, wherein the light is collimated and directed to the diaphragm, wherein the diaphragm blocks a portion of light and allows a portion of the light to pass therethrough, resulting in light that interacts with a sample, producing a darkfield image, and a fluorescent image.

15. The direct-view light optical microscope according to claim 14, wherein the adjustable portion is adjusted by a lever.

16. The direct-view light optical microscope according to claim 14, wherein the filter is removable.

17. The direct-view light optical microscope according to claim 14, wherein the filter filters light of one particular wavelength from white light.

18. The direct-view light optical microscope according to claim 14, further comprising an Acousto-Optical Tunable Filter, wherein the Acousto-Optical Tunable Filter filters incident light, resulting in filtered light, and wherein the Acousto-Optical Tunable Filter is connected to a power source for providing a voltage, wherein a wavelength of the resulting light is tuned by changing the voltage supplied to the Acousto-Optical Tunable Filter, and wherein the resulting light is tuned to a desired wavelength.

19. A method of simultaneous observation of darkfield images and fluorescence comprising:
selecting a fluorescent light filter to filter light, the filter having a diameter (F);
producing illumination from a light source;
directing the illumination to a diaphragm having a variable sized opening, wherein the selected fluorescent light filter is positioned within the diaphragm;
varying the variable sized opening of the diaphragm to control an amount of illumination able to pass through the diaphragm, resulting in light to produce a darkfield image with a diameter (I); and
filtering the light with the fluorescent light filter, resulting in light comprising a beam of filtered light having diameter (F) surrounded by a cylinder of unfiltered light with an outside diameter (I) and an inside diameter (F).

20. The method of the simultaneous observation of darkfield images and fluorescence according to claim 19, wherein the fluorescent light filter is selected based on the desired wavelength of the fluorescent light.

21. The method of the simultaneous observation of darkfield images and fluorescence according to claim 19, wherein the fluorescent light filter is an Acousto-Optical Tunable Filter.

22. The method of the simultaneous observation of darkfield images and fluorescence according to claim 21, further comprising:
coupling the Acousto-Optical Tunable Filter to a power supply, wherein the power supply supplies a voltage across the Acousto-Optical Tunable Filter; and
changing the voltage on the power supply, wherein a wavelength of light allowed through the Acousto-Optical Tunable Filter is tuned by a change in the voltage.

23. The method of the simultaneous observation of darkfield images and fluorescence according to claim 19, further comprising:
directing the unfiltered light to a sample;
directing the filtered light to the sample; and
observing a darkfield image and a fluorescent image produced by the sample.

24. The method of the simultaneous observation of darkfield images and fluorescence according to claim 19, further comprising:
magnifying an image with a compound relay lens, obtaining the image with a camera, the image obtained from observing a darkfield image produced by the unfiltered light and observing a fluorescent image produced by the filtered light; and
transferring the image to a camera and a computer.

25. A method of simultaneous observation of darkfield images and fluorescence comprising:
selecting a fluorescent light filter to filter light, the filter having a diameter (F);
producing illumination from a light source;
directing the illumination to a diaphragm having a variable-sized diameter, wherein the selected fluorescent light filter is positioned within the diaphragm;
varying the variable-sized diameter of the diaphragm to control an amount of illumination able to pass through the diaphragm, resulting in light to produce a darkfield image with a diameter (I);
filtering the light with the fluorescent light filter, resulting in light comprising a beam of filtered light having diameter (F) surrounded by a cylinder of unfiltered light with an outside diameter (I) and an inside diameter (F);
directing the unfiltered light to a sample;
directing the filtered light to a sample; and
observing a darkfield image and a fluorescent image produced by the sample.

\* \* \* \* \*

UNITED STATES PATENT AND TRADEMARK OFFICE
CERTIFICATE OF CORRECTION

PATENT NO. : 7,688,505 B2
APPLICATION NO. : 11/636107
DATED : March 30, 2010
INVENTOR(S) : Vitaly Vodyanoy and Oleg Pustovyy It is certified that error appears in the above-identified patent and that said Letters Patent is hereby corrected as shown below:

TITLE PAGE; IN THE REFERENCES CITED [56]

At the title page, references cited (56), please delete the reference: "3,666,362 to Change" and insert the reference: -- 3,666,362 to Chance --.

Signed and Sealed this

Eleventh Day of May, 2010

David J. Kappos
*Director of the United States Patent and Trademark Office*